(12) United States Patent
Li et al.

(10) Patent No.: US 10,592,242 B2
(45) Date of Patent: Mar. 17, 2020

(54) SYSTEMS AND METHODS FOR RENDERING VECTOR DATA ON STATIC AND DYNAMIC-SURFACES USING SCREEN SPACE DECALS AND A DEPTH TEXTURE

(71) Applicant: Cesium GS, Inc., Exton, PA (US)

(72) Inventors: Kangning Li, North Wales, PA (US); Daniel Bagnell, Exton, PA (US)

(73) Assignee: Cesium GS, Inc., Exton, PA (US)

( * ) Notice: Subject to any disclaimer, the term of this patent is extended or adjusted under 35 U.S.C. 154(b) by 0 days.

(21) Appl. No.: 16/516,997

(22) Filed: Jul. 19, 2019

(65) Prior Publication Data

US 2020/0026516 A1    Jan. 23, 2020

Related U.S. Application Data

(60) Provisional application No. 62/701,099, filed on Jul. 20, 2018.

(51) Int. Cl.
  *G06F 9/30* (2018.01)

(52) U.S. Cl.
  CPC ...... *G06F 9/30036* (2013.01); *G06F 9/30043* (2013.01)

(58) Field of Classification Search
  CPC .......................... G06F 9/30036; G06F 9/30043
  See application file for complete search history.

(56) References Cited

U.S. PATENT DOCUMENTS

| | | | |
|---|---|---|---|
| 6,396,496 B1 * | 5/2002 | Pfister | G06T 13/20 345/420 |
| 2015/0178961 A1 * | 6/2015 | Karras | G06T 11/203 345/442 |

OTHER PUBLICATIONS

Samavati, F. and Runions, A., 2016. Interactive 3D content modeling for digital earth. The Visual Computer, 32(10), pp. 1293-1309.*

Lee, Jiyeong. A 3-D data model for representing topological relationships between spatial entities in built-environments. Diss. The Ohio State University, 2001. pp. 1-192.*

Baig, Siddique Ullah. A Three-step Strategy for Generalization of Three-dimensional Buildings Modelled in City Geographic Markup Language. Diss. Universiti Teknologi Malaysia, 2013. pp. 1-163.*

* cited by examiner

*Primary Examiner* — Sarah Lhymn

(74) *Attorney, Agent, or Firm* — The Marbury Law Group, PLLC

(57) ABSTRACT

Systems, methods, devices, and non-transitory media of various embodiments render vector data on static and dynamic surfaces by a computing device for a graphic display or for a separate computing device and/or algorithm to generate an image. Complex vector data associated with a surface for rendering may be rendered. The complex vector data may be decomposed into one or more vector subunits. A geometry corresponding to a volume and a mathematical description of an extrusion of each corresponding vector subunit may be generated. The volume and the mathematical description of the extrusion may intersect a surface level-of-detail of the surface. The geometry may be rasterized as a screen-space decal. Also, a surface depth texture may be compared for the surface against the extrusion using at least the screen-space decal. In addition, geometry batching may be performed for drawing simultaneously a plurality of the one or more vector subunits.

30 Claims, 10 Drawing Sheets

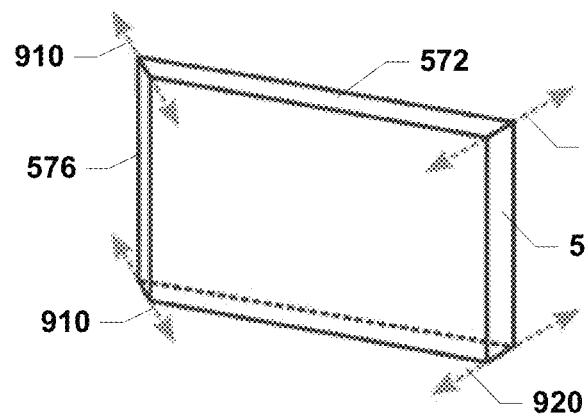
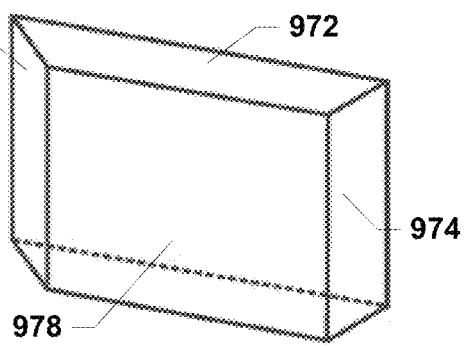
FIG. 9A    FIG. 9B
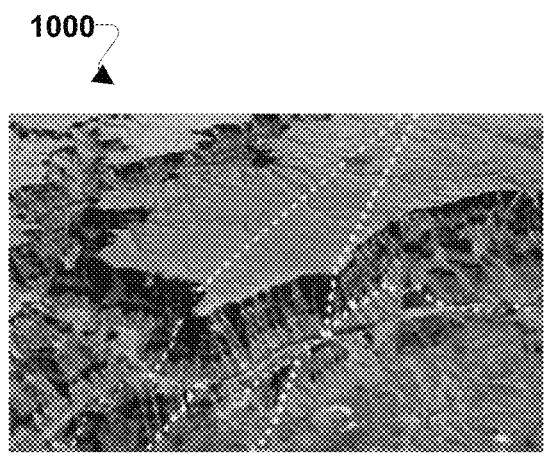
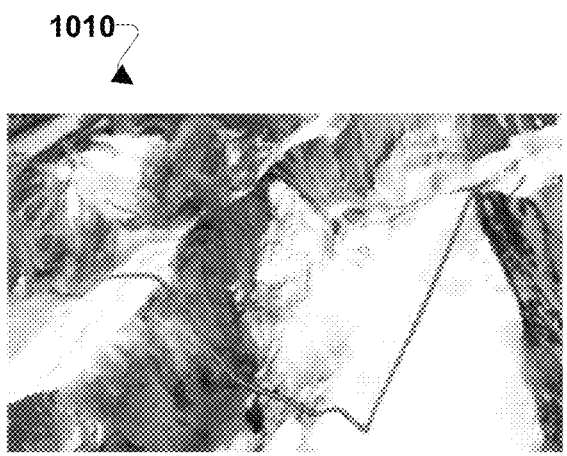
FIG. 10A    FIG. 10B

SYSTEMS AND METHODS FOR RENDERING VECTOR DATA ON STATIC AND DYNAMIC-SURFACES USING SCREEN SPACE DECALS AND A DEPTH TEXTURE

RELATED APPLICATIONS

This application claims priority to U.S. Provisional Application No. 62/701,099 filed on Jul. 20, 2018 entitled "Systems and Methods For Rendering Vector Data On Static And Dynamic Surfaces Using Screen Space Decals And A Depth Texture," the entire contents of which are hereby incorporated by reference.

FIELD

The present disclosure relates to systems and methods for rendering vector data on static and dynamic surfaces.

BACKGROUND

Rendering vector data on top of surfaces is a challenge because the surface may not be precisely known to the rendering computing device. For example, if the rendering is provided by a third-party for a particular application. In addition, the surface shape may change depending on the camera view as with level-of-detail terrain or level-of-detail photogrammetry models. The surface shape may also change regardless of level-of-detail such as for time-dynamic surfaces.

SUMMARY

Various embodiments may include systems, methods, devices, and/or non-transitory processor-readable medium, which may be performed by a computing device. Various embodiments may include rendering vector data on static and dynamic surfaces by a computing device for a graphic display or for a separate computing device and/or algorithm to generate an image. In particular, various embodiments include receiving complex vector data associated with a surface for rendering on the graphic display. The complex vector data may be decomposed into one or more vector subunits. A geometry corresponding to a volume and a mathematical description of an extrusion of each corresponding vector subunit may be generated. The volume and the mathematical description of the extrusion may intersect a surface level-of-detail of the surface. The geometry may be rasterized as a screen-space decal. Also, a surface depth texture may be compared for the surface against the extrusion using at least the screen-space decal. In addition, geometry batching may be performed for drawing simultaneously a plurality of the one or more vector subunits.

In various embodiments, the extrusion of each corresponding vector subunit comprises a set of planes describing a wall. The volume may be a cuboid volume having one dimension substantially smaller than other dimensions thereof. Each vector subunit may be associated with a polyline that lies within the volume. In some embodiments, a plurality of lines may lie within the volume. Having multiple lines within the volume may reduce the total number of volumes that have to be drawn, since having several volumes overlap onscreen may be more expensive to render. Sometimes comparing each point on terrain (determined from depth in the fragment shader) with multiple line segments may be more efficient and reduce operating costs as compared to rending multiple volumes each defining separate line segments. Also, the plurality of lines may be at least one of parallel and no more than two meters apart. The volume may be generated with vertex attributes that describe the vector subunit using a set of planes. For each fragment on the volume, a depth value may be determined relative to the camera of a position on the static or dynamic surface. For example, a globe depth, such as for a globe rendering, may be determined to compute a terrain position in eye space. The determined terrain position may be clipped based on the set of planes from vertex attributes. A distance of the terrain position from the center and ends of the line segment may be determined. A plurality of lines may lie within the volume. Also, the plurality of lines may be at least one of parallel and no more than two meters apart.

Various aspects may include a device including a processor configured with processor-executable instructions to perform operations of any of the methods summarized above. Various aspects may also include a non-transitory processor-readable medium on which is stored processor-executable instructions configured to cause a processor of a device to perform operations of any of the methods summarized above.

BRIEF DESCRIPTION OF THE DRAWINGS

The accompanying drawings, which are incorporated herein and constitute part of this specification, illustrate exemplary embodiments of the claims, and together with the general description given above and the detailed description given below, serve to explain the features of the claims.

FIGS. 9A and 9B illustrate a cuboid volume being transformed using the vertex shader in accordance with various embodiments.

FIGS. 10A and 10B illustrate two on screen views that demonstrate the use of the fragment shader in accordance with various embodiments.

DETAILED DESCRIPTION

Figure 1:
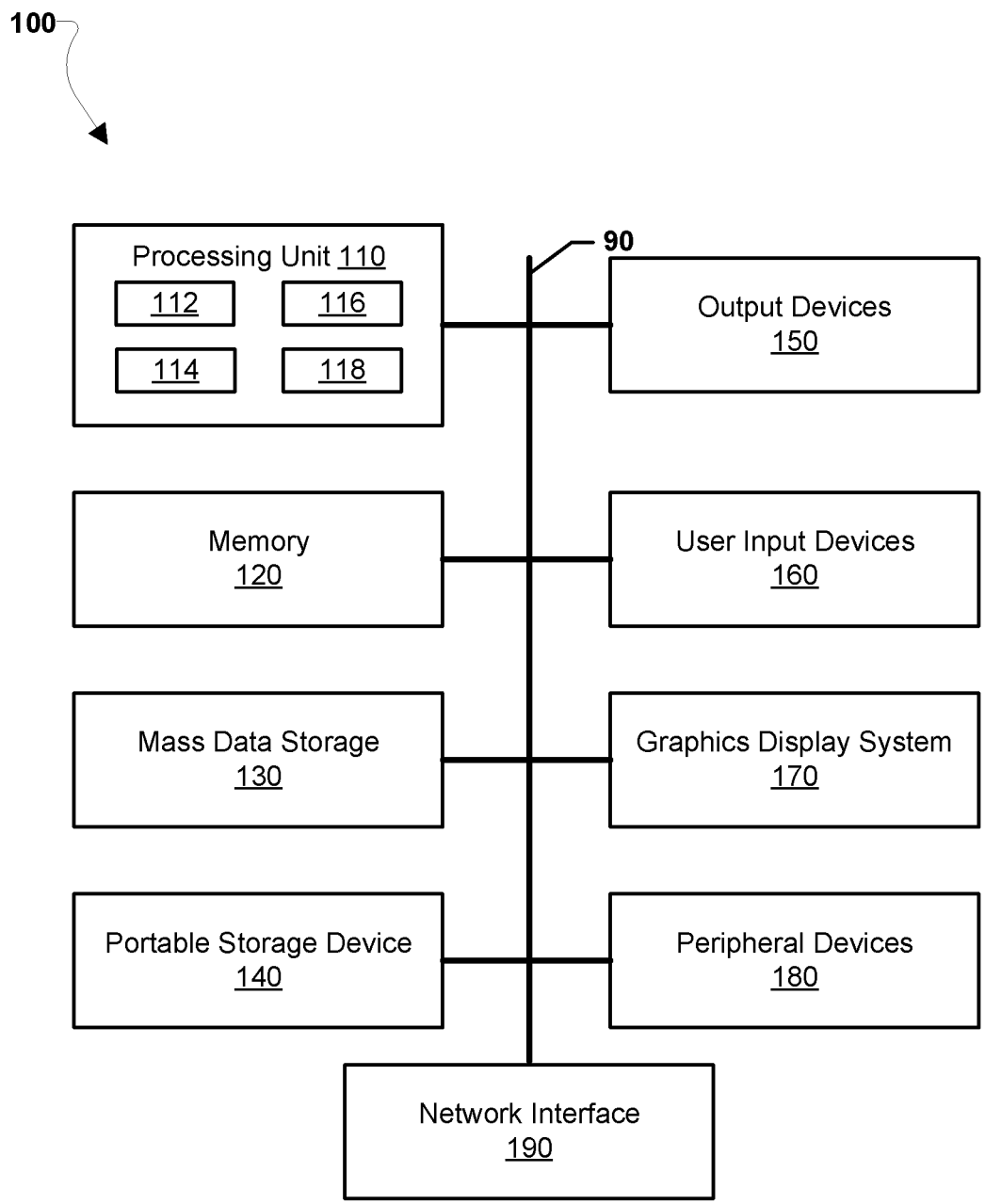
FIG. 1 is a block diagram of an example computing device in accordance with various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The systems, methods, devices, and non-transitory processor-readable medium of various embodiments enable the rendering of vector data on static and dynamic surfaces, which includes decomposing complex vector data into multiple vector subunits (e.g., one or more polylines). Each one of these vector subunits may be defined by a geometry plus a mathematical description thereof. In particular, for each of the vector subunits, the geometry may correspond to a volume associated with the vector subunit and the mathematical description may correspond to a set of planes describing a wall of the volume. The vector subunits may be line segments, simple polygons, point coordinates, or other shapes with compact mathematical definitions that taken together represent polylines, filled polygons, points, text, or other vector data on the surfaces within the scope of the invention. Dynamic surfaces need not have multiple levels-of-detail, such as a simulated water surface or a surface that erodes over time. In some embodiments, the surfaces may have a single, static level-of-detail or the surfaces may have multiple levels-of-detail that are individually dynamic Thus, the dynamic surfaces may include, but are not limited to, level-of-detail surfaces. Although some descriptions herein refer to the surfaces as level-of-detail surfaces, various embodiments are not so limited and work for any combination of separate surfaces that may be static, dynamic, and/or level-of-detail. In some embodiments, the volume and a vector subunit may both intersect all surface levels-of-detail. The method may also include rasterizing each geometry as a screen-space decal. In addition, each fragment may receive the full mathematical description of the extrusion of the vector subunit intersecting all surface levels-of-detail. In some embodiments, the method further includes comparing the surface depth texture for a given surface against the extrusion. In various embodiments, the method compares the extrusion against the surface depth texture for what is currently being viewed. In some embodiments, the method may also (or instead) compare the extrusion against a surface that is not being drawn at all. Thus, any given surface may be a surface that is currently being viewed or may be a surface that is not being drawn at all. In some embodiments, geometry batching is included to further improve performance.

The term "computing device" as used herein refers to any one or all of cellular telephones, smailphones, personal or mobile multi-media players, personal data assistants (PDA's), laptop computers, personal computers, servers, tablet computers, smartbooks, ultrabooks, palm-top computers, multimedia Internet enabled cellular telephones, and similar electronic devices that include a memory and a programmable processor. While specific examples are listed above, the various embodiments are generally useful in any electronic device that includes a processor and executes application programs.

Computer graphics, and especially three-dimensional (also referred to simply as "3D" herein) visualization, is a rapidly developing computing technology finding new applications in many different industries, including geospatial, defense, and entertainment.

One challenge faced in 3D visualization is the complicated nature of 3D objects. Three-dimensional objects generally are formed from a geometry of polygons, often a set of triangles (i.e., a triangle mesh) or quadrilaterals (i.e., a quadrilateral mesh), and textures, often a set of two-dimensional images. A higher quality 3D object often includes large amounts of data that can be spread out over many file locations. As such, high quality 3D images of objects can be difficult to render in a computing device display. Additionally, high quality 3D objects may not be needed in every visualization. For example, when a camera view point for a 3D model is zoomed out sufficiently, a low-quality 3D object may be suitable for rendering. Accordingly, in 3D visualization it can be beneficial to create multiple versions of a 3D object, such as a high-quality version and a low-quality version.

Textures are often used in computer graphics to increase the detail of information on surfaces. Surface information may include base color, static light color/intensity, influence weight for deformation algorithms, and parameters for shading algorithms, such as bump mapping or subsurface scattering.

FIG. 1 is a block diagram of an example computing device 100 suitable for use with the various embodiments. The computing device 100 may be implemented as part of one or more computing systems, networks, servers, or combinations thereof. The computing device 100 may include a control unit 110. The control unit 110 may include, for example, a digital signal processor (DSP) 112, a graphics processor 114, an application processor 116, one or more coprocessors 118 (e.g., vector co-processor) connected to one or more of the processors, memory 120, custom circuitry 122, and system resources 124, all interacting via an interconnection/bus 90. The graphics processor 114 may also be coupled to a display that is part of one or more peripheral devices 180, which may be configured to render images.

Each processor 112, 114, 116, 118 may include one or more cores, and each processor/core may perform operations independent of the other processors/cores. One or more of the processors 112, 114, 116, 118 may be configured with processor-executable instructions to perform operations of methods of various embodiments (e.g., method 1500 described herein with reference to FIG. 15). The processors 112, 114, 116, 118 may be any programmable microprocessor, microcomputer or multiple processor chip or chips that can be configured by software instructions (applications) to perform a variety of functions, including the functions of the various embodiments described above. In some devices, multiple processors may be provided, such as one processor dedicated to graphics processing and one processor dedicated to running other applications. Typically, software applications may be stored in the memory 220 before they are accessed and loaded into one or more of the processors 112, 114, 116, 118. The processors 112, 114, 116, 118 may include internal memory sufficient to store the application software instructions. In many devices, the internal memory may be a volatile or nonvolatile memory, such as flash memory, or a mixture of both. For the purposes of this description, a general reference to memory refers to memory accessible by the processors 112, 114, 116, 118 including internal memory or removable memory plugged into the computing device (e.g., a peripheral device 180) and memory within the processors 112, 114, 116, 118.

Memory 120 may store, in part, instructions and data for execution by the control unit 110. In addition, memory 120 may store the executable code when in operation in accordance with various embodiments. The computing device 100 of FIG. 1 may further includes a mass data storage 130, portable storage device 140, output devices 150, user input devices 160, a graphics display system 170, peripheral devices 180, and a network interface 190.

The components of the computing device 100 are illustrated as being connected via a single bus 90. However, the components of the computing device 100 may be connected through one or more data transport means. The control unit 110 and the memory 120 may be connected via a local microprocessor bus, and the mass data storage 130, peripheral device(s) 180, portable storage device 140, and graphics display system 170 are connected via one or more input/output (I/O) buses.

Mass data storage 130, which can be implemented with a magnetic disk drive, solid state drive, or an optical disk drive, is a non-volatile storage device for storing data and instructions for use by the control unit 110. Mass data storage 130 stores the system software for implementing embodiments of the present disclosure for purposes of loading that software into memory 120.

Portable storage device 140 operates in conjunction with a portable non-volatile storage medium, such as a flash drive, floppy disk, compact disk, digital video disc, or Universal Serial Bus (USB) storage device, to input and output data and code to and from the computing device 100 of FIG. 1. The system software for implementing embodiments of the present disclosure is stored on such a portable medium and input to the computing device 100 via the portable storage device 140.

User input devices 160 can provide a portion of a user interface. User input devices 160 may include one or more microphones, an alphanumeric keypad, such as a keyboard, for inputting alphanumeric and other information, or a pointing device, such as a mouse, a trackball, stylus, or cursor direction keys. User input devices 160 can also include a touch screen. Additionally, the computing device 100 as shown in FIG. 1 includes output devices 150. Suitable output devices 150 include speakers, printers, network interfaces, and monitors.

Graphics display system 170 include a liquid crystal display (LCD) or other suitable display device. Graphics display system 170 is configurable to receive textual and graphical information and processes the information for output to the display device.

Peripheral devices 180 may include any type of computer support device to add additional functionality to the computing device.

The method and systems of the present disclosure can use the same pre-computed geometry for all variations on the surface including levels of detail and may require only one draw call per style within a rendered polyline-on-surface dataset. In various embodiments, having just this single draw call reduces central processing unit (CPU) and graphics processing unit (GPU) overheads. In some embodiments, the method can also render filled and styled polygons and points on surfaces using extrusions of quadrilaterals, triangles, or points instead of line segments. As used herein, an extrusion refers to the rendering of a 3D object from a two-dimensional one by essentially stretching one or more lines out along a new third axis. In this way, a square may be converted into a cube The methods and systems of various embodiments of the present disclosure employ two noted observations. A first of the noted observations is that a line segment on a surface can generally be represented as the intersection between the surface and a virtual quadrilateral wall. A line segment is defined as a vector, having a starting point, a direction, and a length. The intersection of that virtual quadrilateral wall (also referred to herein as just the "wall") with any surface level-of-detail may describe a polyline (i.e., one or more line segments) on that level-of-detail. Thus, in a 3D globe engine, various embodiments may define walls that are perpendicular to the globe's reference ellipsoid (e.g., the Earth's center) such that the wall intersects all surface variations at the same set of latitude/longitude points. A second of the noted observations is that, for every visible point on a surface in a given on-screen view, a 3D position on the surface can be computed using on-screen coordinates and the surface Z-depth for each point, which depth corresponds to a position relative to a front (i.e., foreground) and back (i.e., background) of a screen image.

In accordance with various embodiments, Table 1 below illustrates exemplary code that may be used for determining (i.e., calculating) meters-per-pixel at a given Z-depth.

TABLE 1

```
float czm_metersPerPixelAtDepth(float depthEC)
{
    float distanceToPixel = -depthEC;
    float frustumPlanesTop = tan(0.5 * u_frustumVerticalFieldOfView);
    float frustumPlanesRight = tan(0.5 * u_frustumHorizontalFieldOfView);
    float pixelHeight = 2.0 * distanceToPixel * frustumPlanesTop /
u_viewPortPixelHeight;
    float pixelWidth = 2.0 * distanceToPixel * frustumPlanesRight /
u_viewPortPixelWidth;
    return max(pixelwidth, pixelHeight)i
}
```

Additionally in accordance with various embodiments, Table 2 below illustrates exemplary code that may be used for determining an eye-space coordinate on a surface from window coordinates. The code in Table 2 assumes a function csm_unpackDepth that unpacks depth values from a depth texture.

TABLE 2

```
vec4 czm_windowToEyeCoordinateOnSurface(vec2 windowCoordinate)
{
    float depth = czm_unpackDepth(texture2D(u_depthTexture,
windowCoordinate.xy / u_viewport.zw));
    float x = 2.0 * (windowCoordinate.x - u_viewport.x) / u_viewport.z -
1.0;
    float y = 2.0 * (windowCoordinate.y - u_viewport.y) / u_viewport.w -
1.0;
    float z = (depth - u_viewportTransformation[3][2]) /
u_viewportTransformation[2][2];
    vec4 q = vec4(x, y, z, 1.0);
    float top = tan(0.5 * u_frustumVerticalFieldOfView);
    float bottom = -top;
    float right = tan(0.5 * u_frustumHorizontalFieldOfView);
    float left = -right;
```

TABLE 2-continued

```
float near = u_currentFrustum.x;
float far = u_currentFrustum.y;
q.x = (q.x * (right - left) + left + right) * 0.5;
q.y = (q.y * (top - bottom) + bottom + top) * 0.5;
q.z = (q.z * (near - far) - near - far) * 0.5;
q.w = 1.0;
return q;
}
```

Figure 2A:
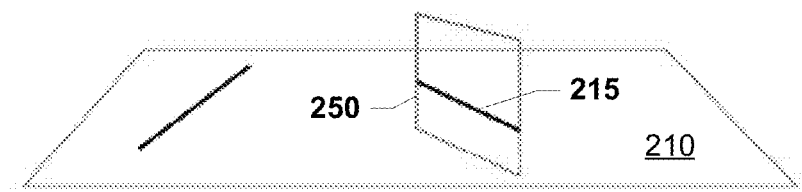
FIGS. 2A-2C illustrate a wall used to describe a polyline in three different screen renderings in accordance with various embodiments.
Figure 2B:
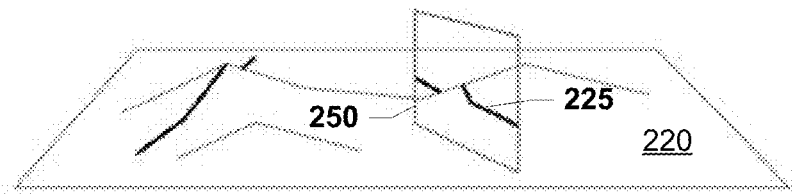
Figure 2C:
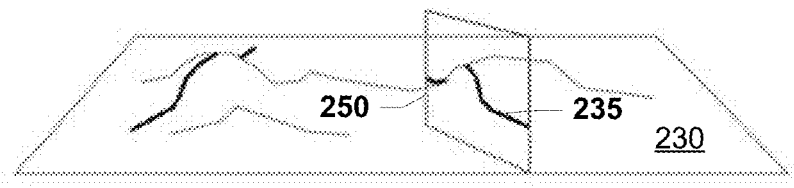

FIGS. 2A-2C illustrate a virtual quadrilateral wall used to describe a polyline in three different screen renderings using different levels of detail for the same terrain in accordance with various embodiments. FIG. 2A shows a wall 250 intersecting a low level-of-detail terrain 210, which intersection is represented by a first polyline 215 that is linear. FIG. 2B shows the wall 250 intersecting a medium level-of-detail terrain 220, which intersection is represented by a second polyline 225, also intersecting the wall 250, that while not linear does not have many angles. FIG. 2C shows the wall 250 intersecting a high level-of-detail terrain 230, which intersection is represented by a third polyline 235, also intersecting the wall 250, that includes multiple bends or angles.

Figure 3:
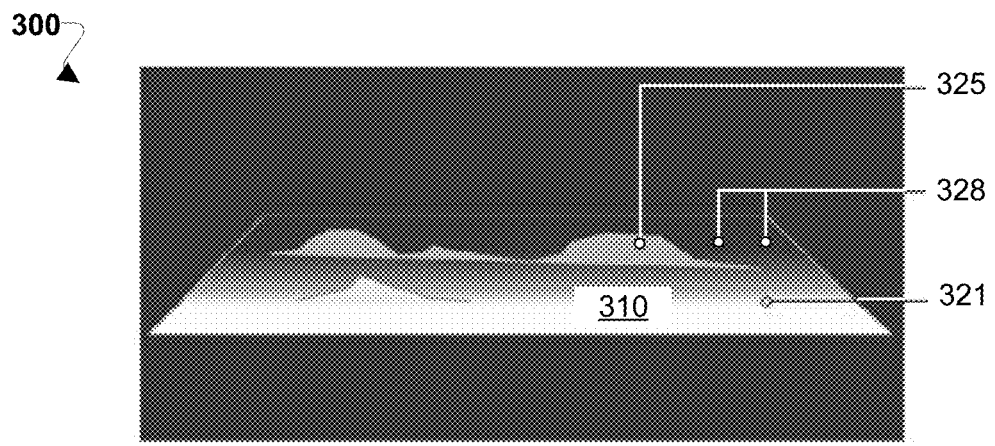
FIG. 3 illustrates an on-screen view including a surface with various different Z-depths in accordance with various embodiments

FIG. 3 illustrates an on-screen view 300 including a surface 310 with three different Z-depths corresponding to four points on the screen. Namely, a first Z-depth 321 corresponding to a single point at a position 0.1 of the maximum depth, a second Z-depth 325 corresponding to a single point at a position 0.5 midway into the maximum depth, and a third Z-depth 328 corresponding to two points at a position 0.8 of the maximum depth.

Figure 4:
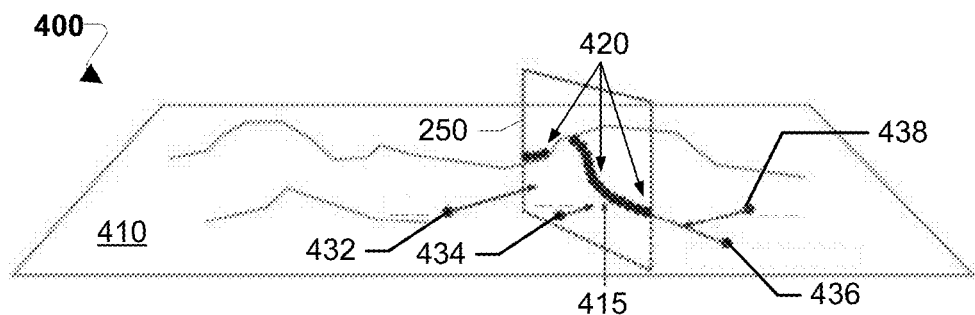
FIG. 4 illustrates an on-screen view including a line segment corresponding to a wall in accordance with various embodiments.

FIG. 4 illustrates an on-screen view 400 including a line segment 420 corresponding to a wall 250 rendered using the two noted observations in accordance with various embodiments. The line segment 420 represents portions of a surface 410 that intersect the wall 250. The line segment 420 may be rendered by comparing each and every surface position (i.e., each pixel or group of pixels) in a given view against the wall 250. Normally, comparing every surface position in a screen rendering would be very difficult and time/resource intensive, particularly when there are multiple line segments, since the comparison needs to know all the details about every line segment for every pixel on the screen. However, various embodiments recognize that most pixels in a view are not part of a given line segment (or other subunit). Thus, various embodiments only attribute mathematical characteristics of a line segment to those pixels that have a threshold likelihood of being associated with the line segment of a particular wall. In this way, various embodiments provide increased efficiencies by avoiding comparisons (i e, minimizing unnecessary use of computational resources) of pixels not likely associated with a particular line segment or wall.

Additionally, various embodiments may use screen decals to represent the walls used to render the geometry of each line segment (or other subunit). In computer graphics, screen decals (hereinafter referred to as just "decals" or in the singular as a "decal") may form an image or texture (e.g., a 3D wall segment) overlaid on top of another texture (e.g., a surface). In addition, various embodiments attribute a mathematical description of a line segment (or other subunit) associated with a decal to each pixel in the decal having a threshold likelihood of being associated with the line segment (or other subunit). Pixels from different parts of the view (i.e., outside the decal) may need a mathematical description of a different line segment or no line segment. Thus, in various embodiments, the comparison as to whether particular pixels are associated with a particular line segment may only need to be performed for portions of the view that are covered by screen-space decals (i.e., the geometry).

With reference to FIG. 4, a first set of pixels 420 located on a line segment 415 are associated with the wall 250. Each of the pixels in the first set of pixels 420 may be attributed mathematical characteristics of the line segment 415. In contrast, various other pixels 432, 434, 438 may be too far from the line segment 415 to be attributed the same mathematical characteristics. Similarly, although pixel 436 may lie in the plane of the wall 250, it too will not be attributed the same mathematical characteristics as the first set of pixels 420 since it is disposed outside the region defining the boundaries of the wall 250.

Although some embodiments have been described with respect to a wall formed as a quadrilateral, it should be understood that walls and/or associated decals in various embodiments may be formed as other polygons (e.g., triangles), shapes, and/or other vector subunits.

Figure 5A:
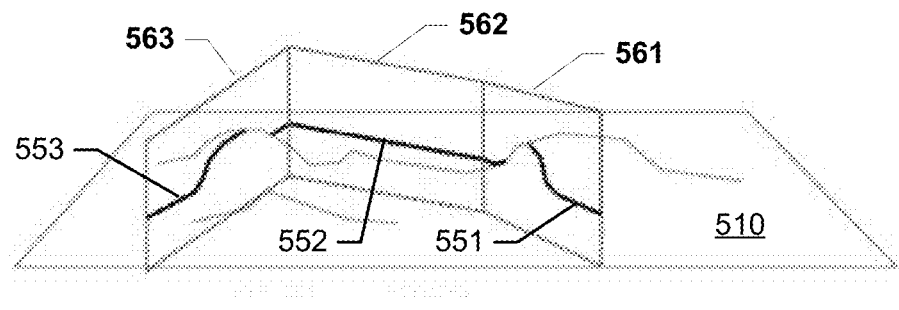
FIGS. 5A-5C illustrate walls defining line segments being converted to volumes in the form of cuboids in accordance with various embodiments.
Figure 5B:
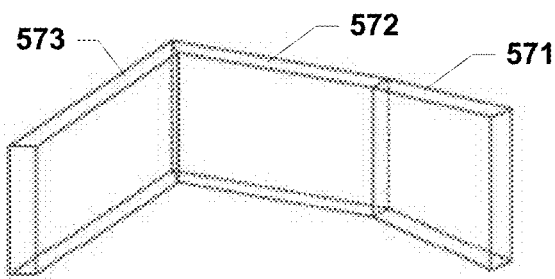
Figure 5C:
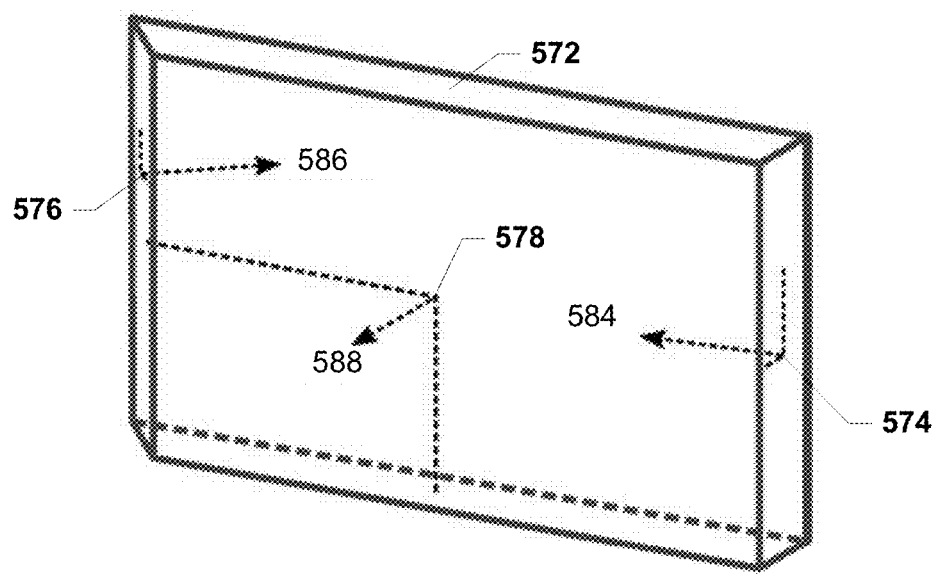

FIGS. 5A-5C illustrate walls defining line segments being converted to volumes in the form of cuboids in accordance with various embodiments.

In FIG. 5A, a first line segment 551 represents portions of a surface 510 that intersect a first wall 561; a second line segment 552 represents portions of the surface 510 that intersect a second wall 562; and a third line segment 553 represents portions of the surface 510 that intersect a third wall 563.

In FIG. 5B, thin cuboid volumes 571, 572, 573 have been generated that correspond to each of the first, second, and third walls 561, 562, 563, respectively, and their associated first, second, and third line segments 551, 552, 553. Each thin cuboid may simulate a constant screen-space line width in pixels. Also, the volume of each cuboid may be widened, depending on how far (i.e., distance) the camera that captured the image was from the surfaces. Additionally, using a volume enables viewing of the line segments from overhead. The geometry of the cuboid volumes 571, 572, 573 may be created with reversed winding order, such that the back-side (i.e., back faces) of each of the cuboid volumes 571, 572, 573 in FIG. 5B corresponds to one of the first, second, and third walls 561, 562, 563, respectively, in FIG. 5A. Such cuboid volumes 571, 572, 573 may be visible even when the view is rendered from inside the volumes, which may also be accomplished by culling front faces instead of back faces when available as a render state of the graphics processor unit (GPU; e.g., 114 in FIG. 1).

FIG. 5C shows a close-up isolated view of the cuboid volume 572 in FIG. 5B. In accordance with various embodiments, vectors representing vertices of the cuboid volume 572 may be used as a mathematical description of a wall (e.g., 562) and the corresponding line segment (e.g., 552) across all the surface levels-of-detail. The wall may be described as having an infinite height using three 3D planes, namely a front plane 574, a back plane 576, and a right plane 578. Also, each of the three 3D planes 574, 576, 578 may mathematically defined by vectors 584, 586, 588 tangential to the surface from a surface point.

Using three 3D planes may allow mitering between cuboid volumes, both to accommodate polyline corners as well as the curvature of a planetoid (e.g., the Earth). Alternatively, for compactness, a 2.5D scene may instead use 2-dimensional values for the plane vectors or even angles, although this may incur additional runtime costs for trigonometry. If mitering of any kind is unnecessary and possible artifacts at the line segment transition points are acceptable, the front and back planes 574, 576 may be omitted altogether in some embodiments. An exemplary 2.5D view may be referred to a "Columbus View," which is a 2.5D perspective view for a map this is laid-out flat and objects with non-zero height are drawn above the map.

An optimization enabled by the various embodiments is geometry batching, which allows many line segments from a large polyline dataset to be drawn simultaneously. Geometry batching enables saturating GPU computational resources for better utilization, but is also important when applied to Web Graphics Library (WebGL) engines due to the additional CPU-side draw call cost added by the WebGL layer.

In some embodiments, geometry batching may be accomplished by combining the vertices from multiple cuboids into a single vertex buffer, with each of the vertices for a given cuboid containing all the planes describing the line segment's wall. In other embodiments, the planes may be stored in a texture and each vertex in the cuboid may carry a batch ID to allow looking up the appropriate set of planes using the texture as a batch table.

Certain implementations operating in small coordinate systems may use planes directly in Hessian-Normal form. However, the method of the present disclosure in various embodiments works with large-magnitude positions on the surface of the Earth and relative to the Earth center, which can cause precision problems (e.g., undesirable artifacts such as jittering or mitering corners not meeting up properly) for traditional Hessian-Normal plane representations using single-precision floating point (e.g., 32 bit). For example, single-precision floating point does not have the precision to properly represent certain large magnitudes that may be needed. Thus, in various embodiments, the planes are instead encoded as a set of vectors and a pair of positions suitable for emulated 64-bit view transformation.

It should be noted that the planes may also be derived entirely in the vertex shader from positions stored as vertex attributes or texture batch table entries. In various embodiments, a mix of points and vectors are selected for data compactness and this information is encoded directly as vertex attributes to reduce texture lookups. Deriving planes directly on the GPU can reduce CPU preprocessing overhead at minimal cost thanks to the GPU's massive parallelism, albeit potentially at the cost of data compactness. The exception to this is for certain embodiments on systems with geometry shaders, which may use adjacent vertex data to reduce the amount of information that must be encoded into either vertex attributes or texture entries.

Figure 6:
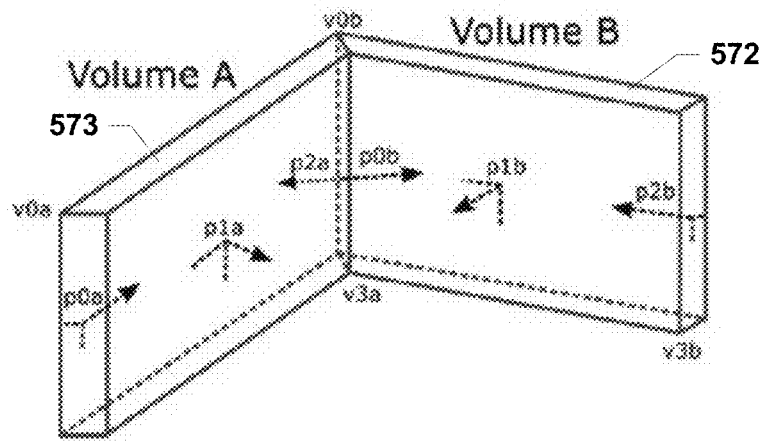
FIG. 6 illustrates a close-up isolated view of cuboid volumes in accordance with various embodiments.

FIG. 6 illustrates a close-up isolated view of the cuboid volumes 572, 573 in FIG. 5B. In FIG. 6, the cuboid volumes 572, 573 are also referred to as "Volume A" and "Volume B," respectively. In accordance with various embodiments, vectors representing vertices of Volume A and Volume B may be used as a mathematical description thereof. Table 3, below provides a basic description for each of the various vertices in FIG. 6.

Figure 7:
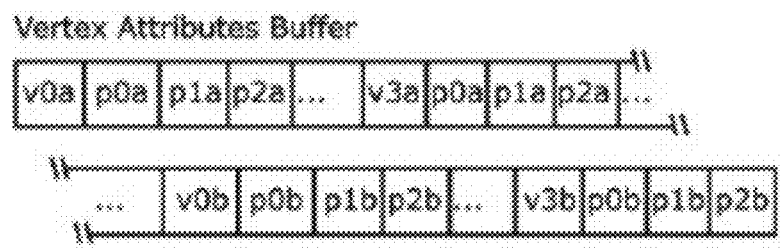
FIG. 7 illustrates a vertex attributes buffer in accordance with various embodiments.

TABLE 3 v0a, v3a - positions on Volume A
v0b, v3b - positions on Volume B
p0a - Volume A back plane
p1a - Volume A right plane
p2a - Volume A front plane
p0b - Volume B back plane
p1b - Volume B right plane
p2b - Volume B front plane FIG. 7 illustrates a vertex attributes buffer in accordance with various embodiments. In particular, the vertex attributes from Table 3 are organized into the vertex attributes buffer in FIG. 7.

Figure 8:
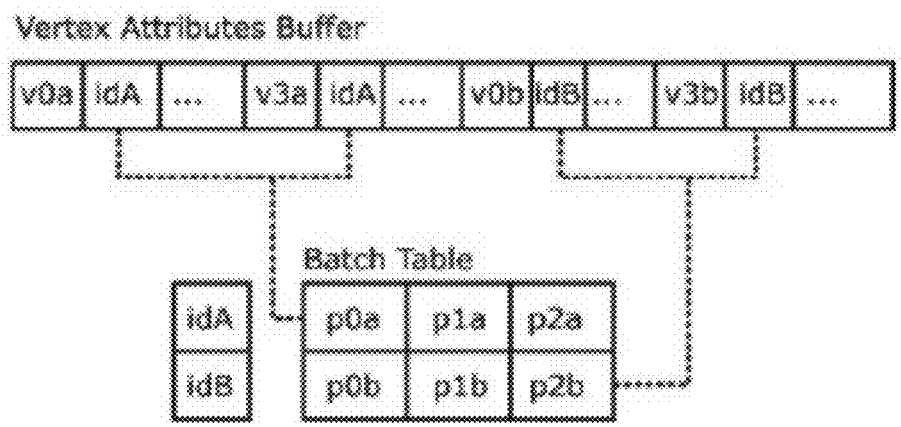
FIG. 8 illustrates a batch table with a corresponding portion of a vertex attributes buffer in accordance with various embodiments.

FIG. 8 illustrates a batch table with a corresponding portion of a vertex attributes buffer in accordance with various embodiments.

In various embodiments, the cuboid may be rasterized as a screen space decal, drawing in front of the surface in screen space regardless of the actual world-space positions. The depth test render state (e.g., of the GPU) may be disabled in various embodiments, but this can also be accomplished by clamping the vertices to the camera near plane, as part of operations referred to as the "vertex shader." The vertex shader may be used to do more than just the aforementioned clamping.

FIGS. 9A and 9B illustrate a cuboid volume being transformed using the vertex shader in accordance with various embodiments.

FIG. 9A illustrates the second cuboid volume 572 from FIGS. 5B, 5C, and 6. The vertex shader, according to certain embodiments, may "push" outwardly the outer walls of the cuboid volume 572 along directions 910, 920 parallel to the front and back planes 574, 576. The magnitude of the push may be determined by the camera's view distance and may simulate an approximately constant screen-space width given the same camera angle but different camera distances.

In accordance with various embodiments, Table 4 below illustrates exemplary code that may be used to perform operations of the vertex shader. The code in Table 4 assumes a function czm_translateRelativeToEye that emulates a 64-bit transform to a coordinate system relative to the camera and a function czm_computePosition that performs this transform in addition to a view transformation.

TABLE 4 attribute vec3 position3DHigh;
attribute vec3 position3DLow;
attribute vec3 normal;
// Planes packed as high-precision positions (high-precision start
position + low precision offset to second position)
and a set of normals.
attribute vec4 startHiAndForwardOffsetX;
attribute vec4 startLoAndForwardOffsetY;
attribute vec4 startNormalAndForwardOffsetZ;
attribute vec3 rightNormal;
attribute vec3 endNormal;
// Planes transferred to Fragment Shader in eye-space Hessian Normal
varying vec4 v_startPlane;
varying vec4 v_endPlane;
varying vec4 v_rightPlane;
void main( )
{
  vec3 ecStart = (czm_modelViewRelativeToEye *
czm_translateRelativeToEye(startHiAndForwardOffsetX.xyz,
startLoAndForwardOffsetY.xyz)).xyz;
  vec3 offset = vec3(startHiAndForwardOffsetX.w,
startLoAndForwardOffsetY.w,
0.0);
offset.z = startNormalAndForwardOffsetZ.w;
offset = czm_normal * offset;
vec3 ecEnd = ecStart + offset;
// end plane
vec3 ecEndNormal = czm_normal * endNormal;
v_endPlane.xyz = ecEndNormal;
v_endPlane.w = -dot(ecEndNormal, ecEnd);
// Right plane
vec3 ecRight = czm_normal * rightNormal;
v_rightPlane.xyz = ecRight;
  v_rightPlane.w = -dot(ecRight, ecStart);
// start plane
vec3 startNormalEC = czm_normal * startNormalAndForwardOffsetZ.xyz;

TABLE 4-continued

```
v_startPlane.xyz = startNormalEC;
v_startPlane.w = -dot(startNormalEC, ecStart);
// Position stuff
vec4 positionRelativeToEye = czm_computePosition( );
// Production implementation pushes along normals according to
angle against forward.
// For brevity, just extend the volume more than necessary.
// Note that this normal is derived from planes in the production code.
positionRelativeToEye.xyz += u_halfLineWidth * 2.0 *
czm_metersPerPixelAtDepth((czm_modelViewProjectionRelativeToEye *
positionRelativeToEye).z) * normal;
    gl_Position = czm_modelViewProjectionRelativeToEye *
positionRelativeToEye;
}
```

The vertex shader may then provide the position of each plane (e.g., 972, 974, 976, 978 in FIG. 9B) and normal values in eye space to operations referred to as the "fragment shader." In the fragment shader, according to various embodiments, each fragment's pixel coordinates may be used to look up the surface depth at the point on the surface "behind" the decal. The depth value and pixel coordinates may be used to compute an eye space position for that point on the surface, which may then be compared against the eye-space front, back, and right planes 974, 976, 978. If the eye-space position on the surface is further than a line-width distance from the right plane 978 and/or is not in between the front and back planes 974, 976, the position on the surface is not considered part of the polyline and the fragment is discarded in various embodiments.

In accordance with various embodiments, Table 5 below illustrates exemplary code that may be used to perform operations of the fragment shader.

TABLE 5

```
varying vec4 v_startPlane;
varying vec4 v_endPlane;
varying vec4 v_rightPlane;
float czm_planeUistance(vec4 plane, vec3 point) {
    return (dot(plane.xyz, point) + plane.w);
}
void main(void)
{
    vec3 eyeCoordinateOnSurface =
czm_windowToEyeCoordinateOnSurface(gl_FragCoord.xy);
    // Check distance of the eye coordinate against the right-facing plane
    bool outOfBounds = abs(czm_planeDistance(v_rightPlane,
eyeCoordinateOnSurface)) > u_halfLineWidth *
czm_metersPerPixelAtDepth(eyeCoordinateOnSurface.z);
    // Check distance of the eye coordinate against the forward-facing and
backfacing planes
    float distanceFromStart = czn_planeUistance(v_startPlane,
eyeCoordinateOnSurface);
    float distanceFromEnd = czm_planeDistance(v_endPlane,
eyeCoordinateOnSurface);
    outOfBounds = outOfBounds II distanceFromStart < 0.0 II
distanceFromEnd < 0.0;
    if (outOfBounds) {
        discard;
    } else i
        gl_FragColc•r = u_lineColor;
    }
}
```

FIGS. 10A and 10B illustrate two on-screen views 1000, 1010 that demonstrate the use of the fragment shader in accordance with various embodiments. In response to a position on the surface being determined to be part of the polyline, the fragment shader may use a distance of that position from the right plane (e.g., 978) and its distances from the front and back planes (e.g., 974, 976) as texture coordinates for styles such as dashes, outlines, or arrows. The distance against the front and back planes may be recomputed after rotating the front and back planes to be orthogonal to the right plane (e.g., 978), which prevents skewing of texture coordinates.

FIGS. 10A and 10B illustrate examples of styling using texture coordinates as described above. In this way, to make a dashed line, the fragment shader uses a measure of how far a point is on the line relative to the line's start in order to determine whether the point is part of the dashed line. The fragment shader should be provided or have access to the measure of how far the point is on the line relative to the line's start. Similarly, to make a line with an outline (i.e., "fill"), the fragment shader uses a measure of how far a point on the line is from the center of the line to determine whether that point is part of the outline. Once again, the fragment shader should be provided or have access to the measure of how far that point is relative to the line's center, which is on a plane that intersects the center of the line.

Figures 11A, 11B:
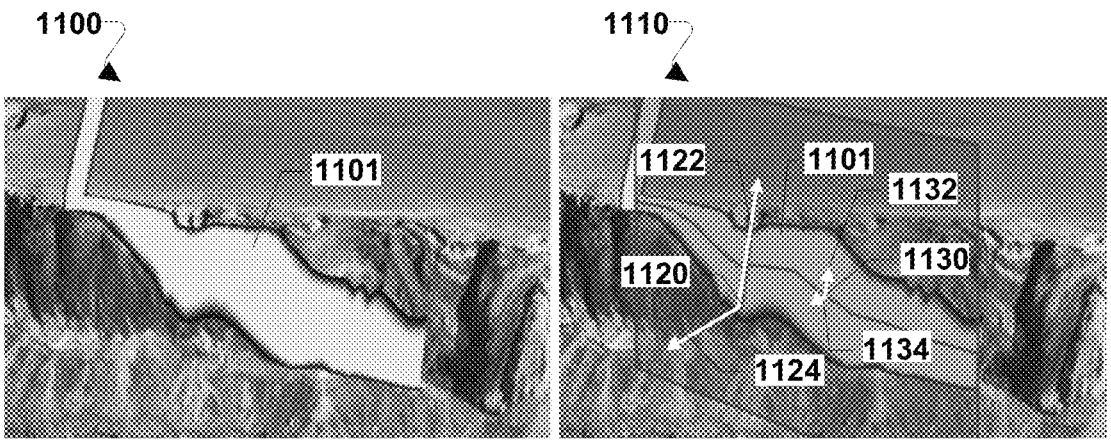
FIGS. 11A and 11B illustrate two on screen views that demonstrate the use of smear reduction on a steep slope 1101 in accordance with various embodiments.

FIGS. 11A and 11B illustrate two on screen views 1100, 1110 that demonstrate the use of smear reduction on a steep slope 1101 in accordance with various embodiments. Screen space techniques may be used to compute surface normals from the fragment shader, which can be used to reduce smearing of wide polylines on steep slopes, using operations referred to as "smear reduction." For certain screen space techniques, a simple point-plane distance check may be used to compare points on the surface to the right plane, with the maximum distance computed from the camera distance to the point on the surface. In various embodiments, the surface normal and right plane normal may enable computation of a vector tangent to the surface at the surface point and pointing towards the right plane, which can be used to perform a ray-plane distance check instead, using a vector tangent to the surface. Points on steep slopes will produce tangent rays that intersect the right plane at a greater distance and be discarded in various embodiments, reducing smear.

In FIG. 11B, a ray-plane intersection for the point at the first origin 1120 of a first two vectors 1122, 1124 shows a very long distance, while rayplane intersection for the point at the second origin 1130 of a second two vectors 1132, 1134 shows a shorter distance. In various embodiments, the point at the second origin 1130 of the second two vectors 1132, 1134 should be part of the line, while the point at the first origin 1120 of the first two vectors 1122, 1124 should not.

Figure 12:
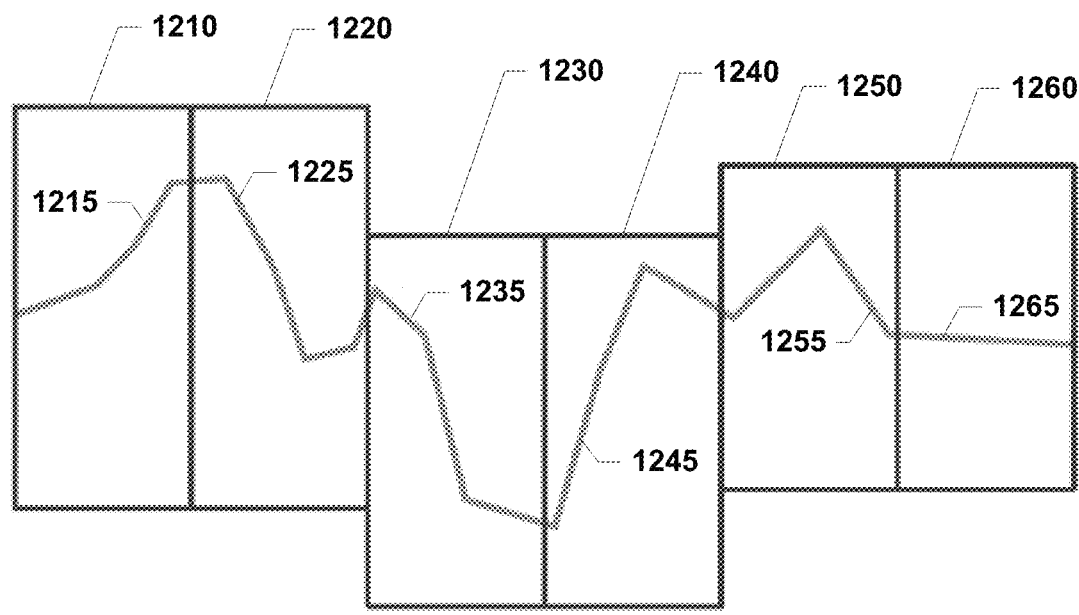
FIG. 12 illustrates a basic side view of volumes that are generously bounding several polylines in accordance with various embodiments.

FIG. 12 illustrates a basic side view of decals 1210, 1220, 1230, 1240, 1250, 1260 drawn from volumes that are generously bounding several polylines 1215, 1225, 1235, 1245, 1255, 1265 (i.e., line segments) in accordance with various embodiments. In particular, the polylines 1215, 1225, 1235, 1245, 1255, 1265 may be clamped to a low-detail surface using the methods described above. The decals 1210, 1220, 1230, 1240, 1250, 1260 may be drawn over a much larger area of the screen than the actual polylines 1215, 1225, 1235, 1245, 1255, 1265 due to the heights of the cuboid volumes; which may be based on a very low-resolution, very low-detail approximation of the surface that may be assumed conservatively and that enclose the actual surface variations.

Figure 13:
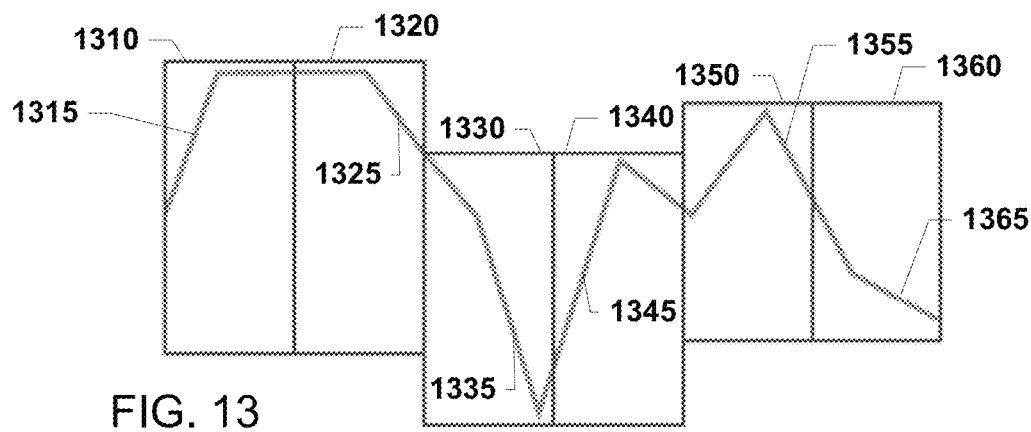
FIG. 13 illustrates a side view of additional bounding volumes in a low-detail environment in accordance with various embodiments

FIG. 13 illustrates a side view of additional bounding decals in a low-detail environment in accordance with various embodiments. With reference to FIG. 13, the polylines 1315, 1325, 1335, 1345, 1355, 1365 exhibit very low detail. Thus, a conservative estimate may be used when forming the decals 1310, 1320, 1330, 1340, 1350, 1360 that bound each of the polylines 1315, 1325, 1335, 1345, 1355, 1365.

Figure 14A:
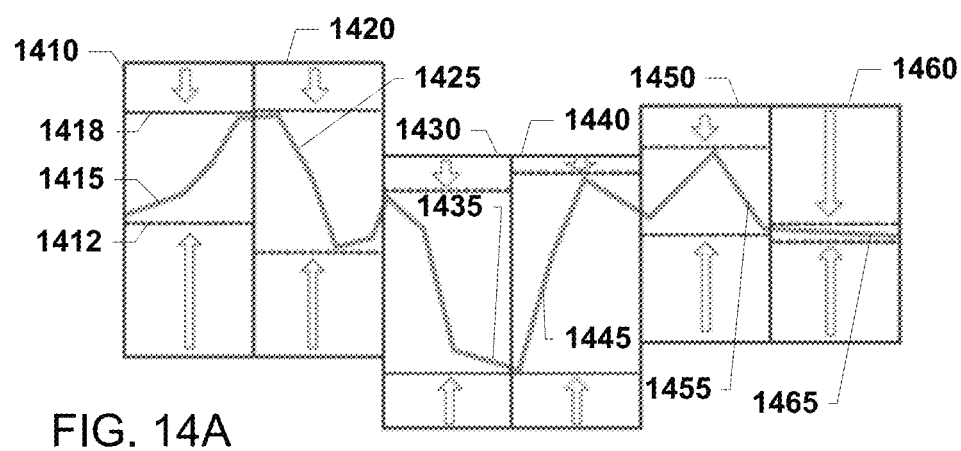
FIGS. 14A-14C illustrate side views of additional bounding volumes in a high-detail environment in accordance with various embodiments.
Figure 14B:
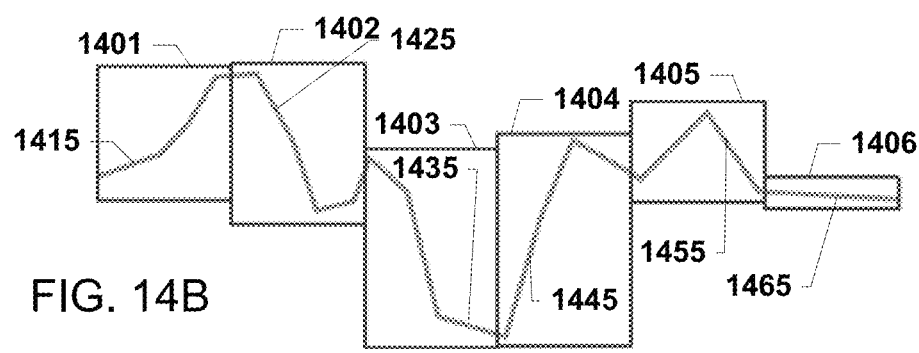
Figure 14C:
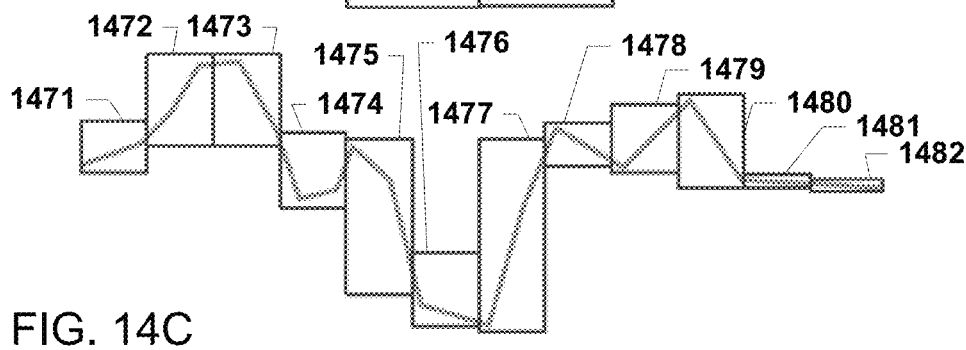

FIGS. 14A-14C illustrate side views of additional bounding decals in a high-detail environment in accordance with various embodiments.

FIG. 14A illustrates how given more information (higher details) about the minimum and maximum heights of the polylines 1415, 1425, 1435, 1445, 1455, 1465 over an area of the surface, various embodiments may lower the top and raise the base of each decal 1410, 1420, 1430, 1440, 1450, 1460 associated with respective cuboid volumes in the vertex shader to more closely bound the surface. In this way, an original upper height of the first decal 1410 may be lowered to a lower height 1418 and an original base height of the first decal 1410 may be raised to a higher height 1412 to form a smaller decal (e.g., 1401 in FIG. 14B) more closely bounding the polyline 1415 therein. Similar adjustments are shown for the other decals 1420, 1430, 1440, 1450, 1460 in accordance with various embodiments.

FIG. 14B illustrates the reduced decals 1401, 1402, 1403, 1404, 1405, 1406 associated with respective cuboid volumes that more closely bound the surface and particularly the polylines (e.g., 1415, 1425, 1435, 1445, 1455, 1465).

FIG. 14C illustrates further reduced decals 1471-1482 with respective cuboid volumes that more closely bound the surface and particularly the polylines (e.g., 1415, 1425, 1435, 1445, 1455, 1465) in accordance with various embodiments. Further subdivision of line segments may further improve fill-rate at the expense of more geometry, allowing fine-tuning of performance for particular customer applications.

Some cases encounter surface restrictions for true 3D surfaces. For example, in applications that involve a surface not representable using 2.5D, undesired drawings on the "undersides" of the surface may be produced. For example, consider a 3D model of a highway overpass—a line drawn on the top side of the 3D surface of the highway overpass will be mirrored on the bottom side (i.e., the underside) of the highway overpass, if the corresponding walls and volumes intersect both the top side and underside of the 3D surface.

In some embodiments, the heights of the volumes may be adjusted to only intersect the top side of the surface. In other embodiments, a single additional plane may be added spanning all volumes that truncate the volumes in the fragment shader to only intersect the top side of the surface. This single additional plane may be implemented either as a uniform or as a batch table entry for a batch ID common across all the volumes.

For applications that require lower precision of the truncation, the camera view angle may also be used in some embodiments such that the polyline is not rendered when the camera is likely to be under the highway overpass, looking upwards at the underside of the 3D surface In some embodiments, a volume with vertex attributes that describe the line segment using a series of planes may be generated for each line segment in a polyline. Then for each fragment on the volume, a depth value relative to the camera of a position on the static or dynamic surface may be determined to compute a terrain position in eye space and clip the computed terrain position based on the planes from the vertex attributes. Using the planes, the terrain position's distance may be determined from the center and ends of the line segment.

Figure 15:
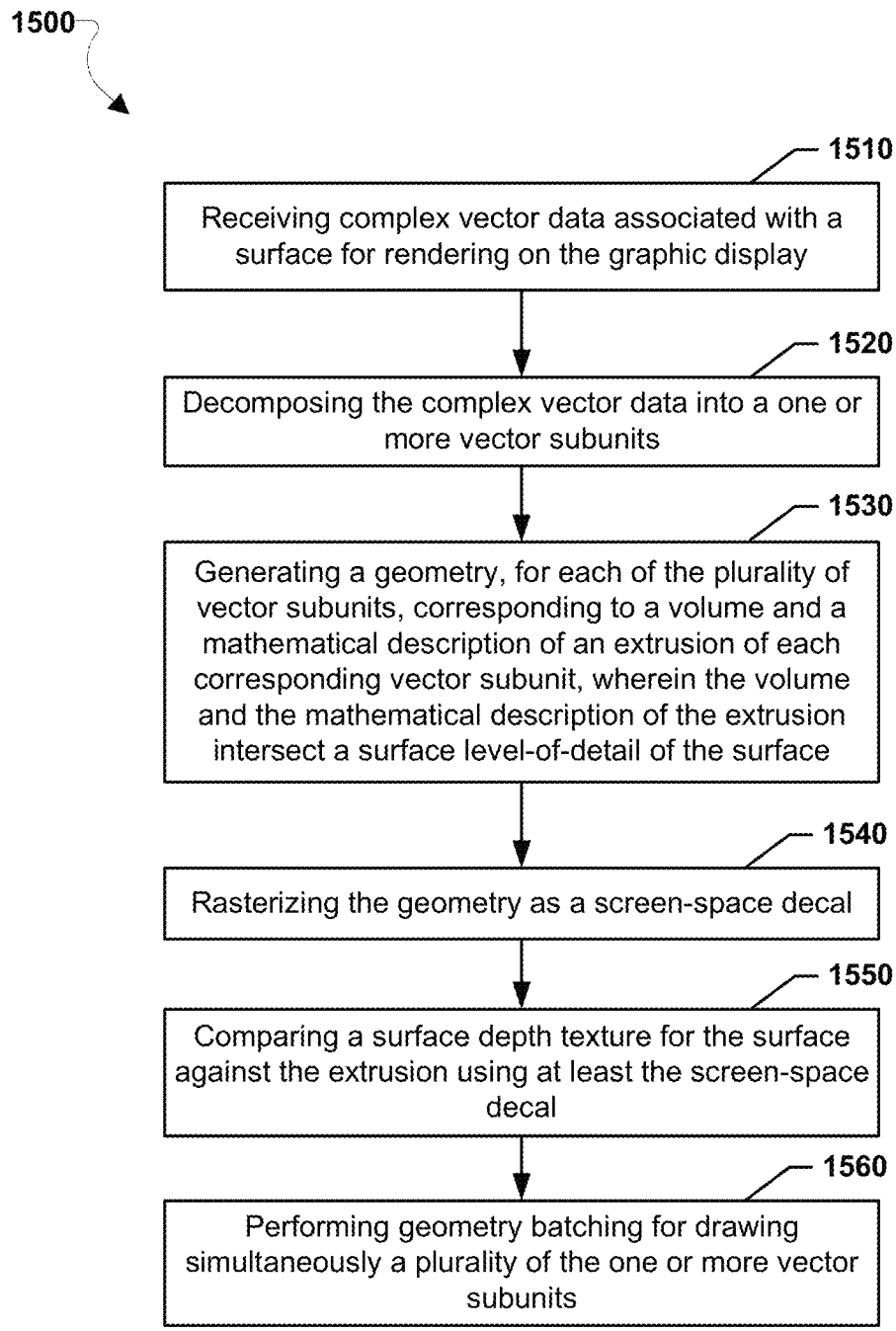
FIG. 15 is a process flow diagram illustrating an embodiment method for rendering vector data on static and dynamic surfaces by a computing device for a graphic display, suitable for use in the various embodiments.

FIG. 15 illustrates an embodiment method 1500 for rendering vector data on static and dynamic surfaces. In various embodiments, the operations of the method 1500 may be performed by a processor (e.g., 112, 114, 116, 118) of a computing device (e.g., 100), a control unit (e.g., 110) thereof, etc.

In block 1510, the processor of the computing device may receive complex vector data associated with one or more surfaces for rendering on the graphic display or for a separate computing device and/or algorithm to generate an image. For example, the computing device may receive the complex vector data from a local memory (e.g., 120), mass data storage (e.g., 130), portable storage device (e.g., 140), a user input device (e.g., 160), a peripheral device (e.g., 180), a network interface (e.g., 190), or other sources.

In block 1520, the computing device may decompose the complex vector data into a plurality of vector subunits, the plurality of vector subunits including multiple pieces of simpler data.

In block 1530, the computing device may generate, for each of the plurality of vector subunits, a geometry comprising a volume and a mathematical description of extruded vector data, the volume and extrusion being computed to intersect any and all surface level-of-detail present.

In block 1540, the computing device may rasterize each geometry as a screen-space decal.

In block 1550, the computing device may compare the surface depth texture for a given surface against the extrusion using at least the screen-space decal.

In block 1560, the computing device may perform geometry batching for drawing simultaneously a number of the vector subunits of the plurality of vector subunits.

In various embodiments, the operations of the method 1500 may be performed continually, such that vector data on static and dynamic surfaces may be rendered repeatedly.

Figure 16:
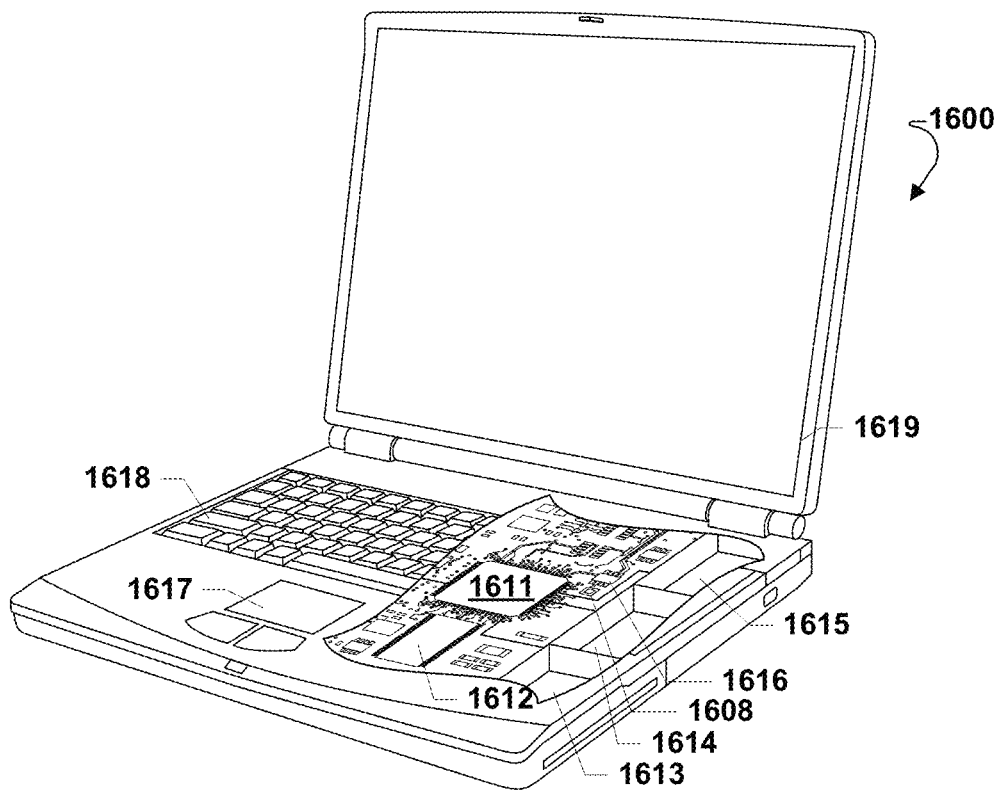
FIG. 16 is a component block diagram of a laptop that is a computing device suitable for use in the various embodiments.

The various embodiments described above may be implemented within a variety of computing devices, such as a laptop computer 1600 illustrated in FIG. 16. Many laptop computers include a touchpad touch surface 1617 that serves as the computer's pointing device, and thus may receive drag, scroll, and flick gestures similar to those implemented on mobile computing devices equipped with a touch screen display and described above. A laptop computer 1600 will typically include a processor 1611 coupled to volatile memory 1612 and a large capacity nonvolatile memory, such as a disk drive 1613 of Flash memory. Additionally, the computer 1600 may have one or more antennas 1608 for sending and receiving electromagnetic radiation that may be connected to a wireless data link and/or cellular telephone transceiver 1616 coupled to the processor 1611. The computer 1600 may also include a floppy disc drive 1614 and a compact disc (CD) drive 1615 coupled to the processor 1611. In a notebook configuration, the computer housing includes the touchpad 1617, the keyboard 1618, and the display 1619 all coupled to the processor 1611. Other configurations of the mobile computing device may include a computer mouse or trackball coupled to the processor (e.g., via a USB input) as are well known, which may also be used in conjunction with the various embodiments.

Figure 17:
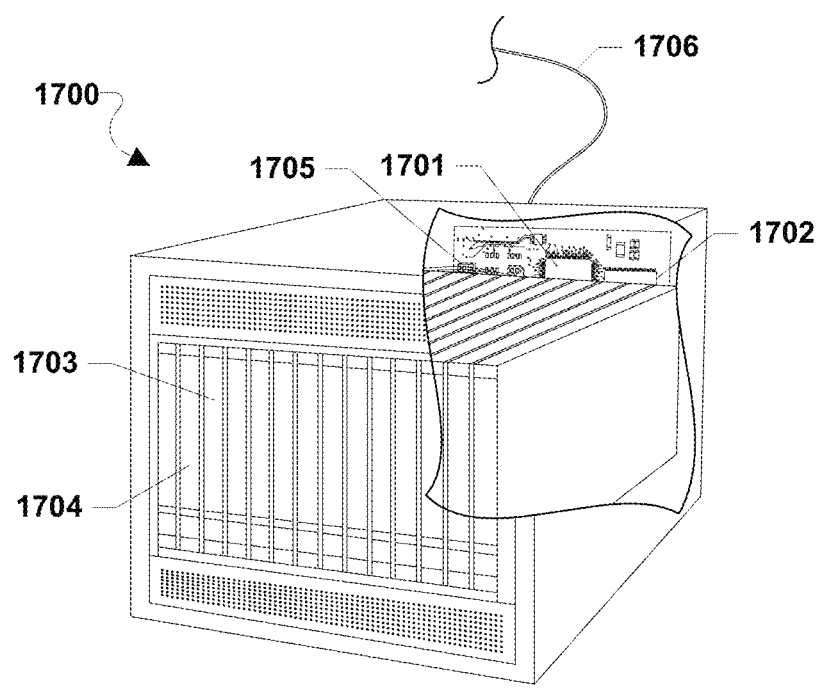
FIG. 17 is a component block diagram of a server that is a computing device suitable for use in the various embodiments.

The various embodiment methods may also be performed partially or completely on a variety of computing devices, such as a server. Such embodiments may be implemented on any of a variety of commercially available server devices, such as the server 1700 illustrated in FIG. 17. Such a server 1700 typically includes a processor 1701 coupled to volatile memory 1702 and a large capacity nonvolatile memory, such as a disk drive 1703. The server 1700 may also include a floppy disc drive, compact disc (CD) or DVD disc drive 1704 coupled to the processor 1701. The server 1700 may also include network access ports 1705 coupled to the processor 1701 for establishing data connections with a network 1706, such as a local area network coupled to other broadcast system computers and servers. The processor 1701 may be any programmable microprocessor, microcomputer or multiple processor chip or chips that may be configured by software instructions (applications) to perform a variety of functions, including the functions of the various embodiments described above. Typically, software applications may be stored in the internal memory 1702, 1703 before they are accessed and loaded into the processor 1701. The processor 1701 may include internal memory sufficient to store the application software instructions.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

As used in this application, the terms "component," "module," "system," "engine," "generator," "unit," "manager" and the like are used interchangeably herein and are intended to include a computer-related entity, such as, but not limited to, hardware, firmware, a combination of hardware and software, software, or software in execution, which are configured to perform particular operations or functions. For example, a component may be, but is not limited to, a process running on a processor, a processor, an object, an executable, a thread of execution, a program, and/or a computer. By way of illustration, both an application running on a computing device and the computing device may be referred to as a component. One or more components may reside within a process and/or thread of execution and a component may be localized on one processor or core and/or distributed between two or more processors or cores. In addition, these components may execute from various non-transitory computer readable media having various instructions and/or data structures stored thereon. Components may communicate by way of local and/or remote processes, function or procedure calls, electronic signals, data packets, memory read/writes, and other known network, computer, processor, and/or process related communication methodologies.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The process flow and block diagrams illustrate the architecture, functionality, and operation of possible implementations of systems, methods and computer program products according to various embodiments of the present technology. In this regard, each block in the process flow or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or process flow illustration, and combinations of blocks in the block diagrams and/or process flow illustration, can be implemented by special purpose hardware-based systems that perform the specified functions or acts, or combinations of special purpose hardware and computer instructions.

The hardware used to implement the various illustrative logics, logical blocks, modules, and circuits described in connection with the embodiments disclosed herein may be implemented or performed with a general purpose processor, a GPU, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a multiprocessor, but, in the alternative, the processor may be any conventional processor, controller, microcontroller, or state machine. A processor may also be implemented as a combination of computing devices, e.g., a combination of a DSP and a multiprocessor, a plurality of multiprocessors, one or more multiprocessors in conjunction with a DSP core, or any other such configuration. Alternatively, some steps or methods may be performed by circuitry that is specific to a given function.

In one or more exemplary embodiments, the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module, which may reside on a non-transitory computer-readable or processor-readable medium. Non-transitory computer-readable or processor-readable medium may be any storage media that may be accessed by a computer or a processor. By way of example but not limitation, such non-transitory computer-readable or processor-readable medium may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable medium. Additionally, the operations of a method or algorithm may reside as one or any combination or set of codes and/or instructions on a non-transitory processor-readable medium and/or computer-readable medium, which may be incorporated into a computer program product.

If implemented in software, the functions described may be stored as one or more instructions or code for carrying out operations of aspects of various embodiments, which may be written in any combination of one or more programming languages, including an object oriented programming language such as Java, Smalltalk, C++ or the like and conventional procedural programming languages, such as the "C" programming language or similar programming languages. Such code may execute entirely on a computing device as a stand-alone software package, partly on the computing device and partly on one or more remote computing devices (e.g., a server) or entirely on the remote one or more remote computing devices. In the latter scenario, the remote one or more remote computing devices may be connected to the initial computing device through any type of network, including a local area network (LAN) or a wide area network (WAN), or the connection may be made to an external computing device (for example, through the Internet using an Internet Service Provider).

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the language of the claims and the principles and novel features disclosed herein.

What is claimed is:

1. A method for rendering vector data on static and dynamic surfaces by a computing device, the method comprising:
    receiving, by a processor of the computing device, vector data associated with a surface for rendering; and
    performing, by the processor, geometry batching for drawing, in parallel, multiple vector subunits, wherein drawing the multiple vector subunits includes:
        decomposing, by the processor, the vector data into the multiple vector subunits;
        generating, by the processor for each of the multiple vector subunits, a geometry an extrusion associated with each of the multiple vector subunits, wherein each geometry defines an outer boundary of a volume within which one or more of the vector subunits lie, wherein each extrusion is a mathematical description of a three-dimensional projection of a corresponding one of the vector subunits onto the outer boundary of the volume, wherein the outer boundary of the volume and the extrusion intersect the surface;
        rasterizing, by the processor, the geometry as a screen-space decal;
        determining, by the processor, whether points associated with the screen-space decal are coincident with each of the vector subunits using a screen space depth of the points relative to the extrusion; and
        drawing, by the processor, individual ones of the points associated with the screen-space decal determined to be coincident with the extrusion.

2. The method of claim 1, wherein the extrusion of each of the multiple vector subunits comprises a set of planes defining a wall.

3. The method of claim 1, wherein the volume is a cuboid volume having one dimension substantially smaller than other dimensions thereof.

4. The method of claim 1, wherein each vector subunit is associated with a polyline that lies within the volume.

5. The method of claim 1, wherein the geometry is generated with vertex attributes that describe the vector subunit using a set of planes.

6. The method of claim 1, further comprising:
    determining the screen space depth of each position on the surface relative to a camera point of view.

7. The method of claim 6, further comprising:
    limiting the positions on the surface for which the screen space depth of each position is determined based on the screen space decal.

8. The method of claim 7, further comprising:
    determining a distance of the positions on the surface from a center and ends of a line segment.

9. The method of claim 1, wherein a plurality of lines lie within the volume.

10. The method of claim 9, wherein the plurality of lines are at least one of parallel and no more than two meters apart.

11. A device, comprising:
    a graphic display; and
    a processor connected to the graphic display, wherein the processor is configured with processor executable instructions to perform operations comprising:
        receiving vector data associated with a surface for rendering on the graphic display; and
        performing geometry batching for drawing, in parallel, multiple vector subunits, wherein performing geometry batching includes:
            decomposing the vector data into the multiple vector subunits;
            generating, for each of the multiple vector subunits, a geometry and an extrusion associated with each of the multiple vector subunits, wherein each geometry defines an outer boundary of a volume within which one or more of the vector subunits lie, wherein each extrusion is a three-dimensional projection of a corresponding one of the vector subunits onto the outer boundary of the volume, wherein the outer boundary of the volume and the extrusion intersect the surface;
            rasterizing the geometry as a screen-space decal;
            determining whether points associated with the screen-space decal are coincident with each of the vector subunits using a screen space depth of the points relative to the extrusion; and
            drawing individual ones of the points associated with the screen-space decal determined to be coincident with the extrusion.

12. The device of claim 11, wherein the processor is further configured with processor-executable instructions such that the extrusion of each of the multiple vector subunits comprises a set of planes defining a wall.

13. The device of claim 11, wherein the processor is further configured with processor-executable instructions such that the volume is a cuboid volume having one dimension substantially smaller than other dimensions thereof.

14. The device of claim 11, wherein the processor is further configured with processor-executable instructions such that each vector subunit is associated with a polyline that lies within the volume.

15. The device of claim 11, wherein the processor is further configured with processor-executable instructions such that the geometry is generated with vertex attributes and/or batch table entries that describe the vector subunit using a set of planes.

16. The device of claim 11, wherein the processor is further configured with processor-executable instructions to:
    determine the screen space depth of each position on the surface relative to a camera point of view.

17. The device of claim 16, wherein the processor is further configured with processor-executable instructions to:
    limit the positions on the surface for which the screen space depth of each position is determined based on the screen space decal.

18. The device of claim 17, wherein the processor is further configured with processor-executable instructions to:
    determine a distance of the positions on the surface from a center and ends of a line segment.

19. The device of claim 11, wherein the processor is further configured with processor-executable instructions such that a plurality of lines lie within the volume.

20. The device of claim 19, wherein the processor is further configured with processor-executable instructions such that the plurality of lines are at least one of parallel and no more than two meters apart.

21. A non-transitory processor-readable medium having stored thereon processor executable instructions configured to cause a processor of a computing device to perform operations comprising:
    receiving vector data associated with a surface for rendering; and
    performing geometry batching for drawing, in parallel, multiple vector subunits, wherein performing geometry batching includes:
        decomposing the vector data into the vector subunits;
        generating, for each of the multiple vector subunits, a geometry and an extrusion associated with each of the multiple vector subunits, wherein each geometry defines an outer boundary of a volume within which one or more of the vector subunits lie, wherein each extrusion is a three-dimensional projection of a corresponding one of the vector subunits onto the outer boundary of the volume, wherein the outer boundary of the volume and the extrusion intersect the surface;
        rasterizing the geometry as a screen-space decal;
        determining whether points associated with the screen-space decal are coincident with each of the vector subunits using a screen space depth of the points relative to the extrusion; and
        drawing individual ones of the points associated with the screen-space decal determined to be coincident with the extrusion.

22. The non-transitory processor-readable medium of claim 21, wherein the stored processor-executable instructions are configured to cause the processor of the computing device to perform operations such that the extrusion of each of the multiple vector subunits comprises a set of planes defining a wall.

23. The non-transitory processor-readable medium of claim 21, wherein the stored processor-executable instructions are configured to cause the processor of the computing device to perform operations such that the volume is a cuboid volume having one dimension substantially smaller than other dimensions thereof.

24. The non-transitory processor-readable medium of claim 21, wherein the stored processor-executable instructions are configured to cause the processor of the computing device to perform operations such that each vector subunit is associated with a polyline that lies within the volume.

25. The non-transitory processor-readable medium of claim 21, wherein the stored processor-executable instructions are configured to cause the processor of the computing device to perform operations such that the geometry is generated with vertex attributes and/or batch table entries that describe the vector subunit using a set of planes.

26. The non-transitory processor-readable medium of claim 21, wherein the stored processor-executable instructions are configured to cause the processor of the computing device to:
    determine the screen space depth of each position on the surface relative to a camera point of view.

27. The non-transitory processor-readable medium of claim 26, wherein the stored processor-executable instructions are configured to cause the processor of the computing device to:
    limit the positions on the surface for which the screen space depth of each position is determined based on the screen space decal.

28. The non-transitory processor-readable medium of claim 27, wherein the stored processor-executable instructions are configured to cause the processor of the computing device to:
    determine a distance of the positions on the surface from a center and ends of a line segment.

29. The non-transitory processor-readable medium of claim 21, wherein the stored processor-executable instructions are configured to cause the processor of the computing device to perform operations such that a plurality of lines lie within the volume.

30. The non-transitory processor-readable medium of claim 29, wherein the stored processor-executable instructions are configured to cause the processor of the computing device to perform operations such that the plurality of lines are at least one of parallel and no more than two meters apart.

* * * * *